United States Patent [19]
Modi et al.

[11] Patent Number: 5,653,987
[45] Date of Patent: Aug. 5, 1997

[54] LIQUID FORMULATIONS FOR PROTEINIC PHARMACEUTICALS

[76] Inventors: Pankaj Modi, 1928 Main St. W., Apt 608, Hamilton, Ontario, Canada, L8S 1J4; Subash Chandarana, 2259 Kirkburn Drive, Burlington, Ontario, Canada, L7P 4E8

[21] Appl. No.: 442,358

[22] Filed: May 16, 1995

[51] Int. Cl.$^6$ ................................................ A61K 38/00
[52] U.S. Cl. ..................... 424/400; 424/434; 424/455; 514/946; 514/947
[58] Field of Search ............................ 424/400, 434, 424/455; 514/946, 947

[56] References Cited

U.S. PATENT DOCUMENTS

| | | | |
|---|---|---|---|
| 4,690,952 | 9/1987 | Kagatani et al. | 514/808 |
| 4,900,730 | 2/1990 | Miyauchi | 514/12 |
| 5,206,219 | 4/1993 | Desai | 424/455 |
| 5,346,701 | 9/1994 | Heiber et al. | 424/435 |
| 5,447,729 | 9/1995 | Belenduik et al. | 424/490 |
| 5,482,706 | 1/1996 | Igari et al. | 424/85.7 |

*Primary Examiner*—Amy Hulina

[57] ABSTRACT

A liquid pharmaceutical agent formulation suitable for oral or nasal delivery comprises a proteinic pharmaceutical agent, water and at least two absorption enhancing compounds. The absorption enhancing compounds are selected from sodium salicylate, sodium lauryl sulphate, disodium ethylenediaminetetraacetic acid (disodium EDTA), oleic acid, linoleic acid, monoolein, lecithin, lysolecithin, deoxycholate, sodium deoxycholate, chenodeoxycholate, taurodeoxycholate, glycochenodeoxycholate, polyoxyethylene X-lauryl ether wherein X is from 9 to 20, sodium tauro-24, 25-dihydrofusidate, polyoxyethylene ether, polyoxyethylene sorbitan esters, p-t-octylphenoxypolyoxyethylene, N-lauryl-β-D-maltopyranoside, 1-dodecylazacycloheptane-2-azone and phospholipids, wherein the amount of each of the absorption enhancing compounds is present in a concentration of from 1 to 10 wt./wt. % of the total formulation. Preferably each of the absorption enhancing compounds is present in a concentration of from 1.5 to 3.5 wt./wt. % The formulation is particulary adapted to oral delivery of insulin.

13 Claims, No Drawings

LIQUID FORMULATIONS FOR PROTEINIC PHARMACEUTICALS

TECHNICAL FIELD

The present invention relates to an improved delivery system for the administration of pharmaceuticals, e.g. peptidic drugs, vaccines and hormones. In particular it relates to insulin, vaccines and hormones which may be orally administered.

BACKGROUND

In the treatment of diabetes, current subcutaneous insulin therapy is limited by the delayed time of onset and time of peak action for the insulin, inability to accommodate changing insulin requirements, e.g. during exercise or meals, and by the large inter- and intra-subject coefficient of variation of absorption and insulin action. Oral delivery of insulin would overcome many of the disadvantages of the subcutaneous delivery system.

The inability of subcutaneous insulin delivery to effectively and safely control glucose levels has encouraged exploration of alternate, less painful methods of delivery that might provide a faster rate of insulin absorption and a relatively short half life. Oral administration of insulin to treat diabetes is likely to be attractive because of its virtual lack of toxicity and its inherent clinical applicability in the reduction in severity of lymphocytic infiltration of pancreatic islets. Furthermore, it has been shown that splenic T-cells from animals orally treated with insulin adoptively transfer protection against diabetes, which indicates that oral insulin generates active cellular mechanisms that suppress disease. Such results suggest that oral insulin affects diabetes and the pancreatic cellular inflammatory process and raises the possibility that oral administration of insulin may provide a new approach for the treatment of autoimmune diabetes.

As indicated, oral delivery of insulin would have many benefits. Oral delivery is also a preferred method of delivering many other therapeutic or pharmaceutical agents. In some instance, even nasal delivery is preferred from a patient point of view because it is not painful like subcutaneous administration and it may be easily self-administered. Nasal delivery of therapeutic agents has the disadvantage that the amount of agent (dose) delivered varies from one dose to another, for a variety of reasons. For example, the lining of the nose is sensitive and sneezing or dripping as a result of irritation of the lining causes loss of usable therapeutic agent. Oral delivery of therapeutic or pharmaceutical agents overcome these difficulties. Even so, if a nasal delivery method is desired, an improved formulation would be helpful.

Effective oral delivery of a pharmaceutical agent requires that the agent has sufficient solubility in the stomach and intestinal lumen and the ability to pass through the intestinal wall. Many peptidic drugs have extremely poor absorption in the gastrointestinal tract and tend to degrade quickly. For example insulin, when introduced orally, has extremely poor absorption in the gastrointestinal tract, tends to degrade quickly, and thus has no metabolic effect on blood glucose levels.

M. Kidron, H. Bar-on, E. M. Berry and E. Ziv in Life Sciences, vol 29, pp 803–9 (1981) and vol 31, pp 2837–41 (1982) have experimented in small animals, with surgical delivery of insulin to the small intestine of a composition of 5 wt. % of an absorption enhancer, e.g. sodium cholate, 2 wt% soyabean trypsin inhibitor and 15 IU of insulin. Such a composition had a metabolic effect on blood sugar level, i.e reduced the blood sugar level by about 30%. However a large amount of insulin was required to produce this effect. The method is obviously not practical in humans and the amount of insulin required would be prohibitively expensive.

A composition which provides effective and practical oral or for some compositions, nasal delivery of pharmaceutical agents has been found.

DISCLOSURE OF INVENTION

Accordingly the present invention provides a liquid pharmaceutical agent formulation suitable for oral or nasal delivery comprising a proteinic pharmaceutical agent, water and at least two absorption enhancing compounds selected from the group consisting of sodium salicylate, sodium lauryl sulphate, disodium ethylenediaminetetraacetic acid (disodium EDTA), oleic acid, linoleic acid, monoolein, lecithin, lysolecithin, deoxycholate, sodium deoxycholate, chenodeoxycholate, taurodeoxycholate, glycochenodeoxycholate, polyoxyethylene X-lauryl ether wherein X is from 9 to 20, sodium tauro-24, 25-dihydrofusidate, polyoxyethylene ether, polyoxyethylene sorbitan esters, p-t-octylphenoxypolyoxyethylene, N-lauryl-β-D-maltopyranoside, 1-dodecylazacycloheptane-2-azone and phospholipids, wherein the amount of each of the absorption enhancing compounds is present in a concentration of from 1 to 10 wt./wt. % of the total formulation.

Sodium lauryl sulphate is sometimes referred to as sodium dodecylsulphate.

In a preferred embodiment the concentration of each of the absorption enhancing compounds is from 1 to 5 wt./wt. % and especially from 1.5 wt./wt. % to 3.5 wt./wt. %

In a preferred embodiment the absorption enhancing compounds are selected from a combination of deoxycholate, chenodeoxycholate, and polyoxyethylene 9-lauryl ether, a combination of sodium salicylate, deoxycholate, chenodeoxycholate, and polyoxyethylene 9-lauryl ether, a combination of sodium deoxycholate, chenodeoxycholate, polyoxyethylene 9-lauryl ether and monoolein, a combination of deoxycholate, chenodeoxycholate and sodium salicylate, a combination of deoxycholate, sodium salicylate and sodium lauryl sulphate, a combination of deoxycholate, chenodeoxycholate, polyoxyethylene 9-lauryl ether and sodium tauro-24, 25-dihydrofusidate, a combination of sodium deoxycholate, chenodeoxycholate, polyoxyethylene 9-lauryl ether and sodium tauro-24, 25-dihydrofusidate, a combination of deoxycholate, chenodeoxycholate, taurodeoxycholate, polyoxyethylene 9-lauryl ether and monoolein, a combination of chenodeoxycholate, glycochenodeoxycholate, polyoxyethylene 9-lauryl ether and sodium tauro-24, 25-dihydrofusidate, a combination of chenodeoxycholate, sodium lauryl sulphate and disodium EDTA, a combination of deoxycholate, chenodeoxycholate, polyoxyethylene 9-lauryl ether and disodium EDTA, a combination of sodium salicylate, disodium EDTA and polyoxyethylene 9-lauryl ether, a combination of monoolein, oleic acid and polyoxyethylene sorbitan ester, a combination of monoolein, oleic acid, polyoxyethylene sorbitan ester and sodium lauryl sulphate, and a combination of linoleic acid, monoolein and sodium salicylate.

A preferred polyoxyethylene sorbitan ester is available under the trade mark Tween 80.

In one embodiment one of the enhancing compounds is polyoxyethylene X-lauryl ether, wherein X is 9 or 10.

In another embodiment the phospholipid is selected from the group consisting of lecithin, lysolecithin, sphingomyelin, phosphatidylcholine, cephalin and phosphatidylethanolamine.

The most preferred absorption enhancing compounds are deoxycholate, chenodeoxycholate, polyoxyethylene 9-lauryl ether, sodium salicylate, monoolein and sodium tauro-24, 25-dihydrofusidate. These in particular, when combined with each other, or with others of the named absorption enhancing compounds, are the most effective.

Preferred combinations are i) deoxycholate, chenodeoxycholate and sodium salicylate, ii) sodium salicylate, deoxycholate and sodium lauryl sulphate, iii) chenodeoxycholate, sodium lauryl sulphate and disodium EDTA and iv) monoolein, oleic acid and polyoxyethylene sorbitan ester, v) deoxycholate, chenodeoxycholate and polyoxyethylene 9-lauryl ether. The most preferred combination is deoxycholate, chenodeoxycholate and polyoxyethylene 9-lauryl ether.

For insulin-containing compositions, it is preferred that the composition also contains at least one inorganic salt which opens channels in the gastrointestinal tract and may provide additional stimulation to release insulin. Non-limiting examples of inorganic salts are sodium, potassium, calcium and zinc salts, especially sodium chloride, potassium chloride, calcium chloride, zinc chloride and sodium bicarbonate.

It is also preferred that the composition contain at least one protective polymer for slow release of the pharmaceutical agent. Preferred protective polymers are polyvinyl alcohol, polyethylene glycol, and gelatin.

It will be recognized by those skilled in the art that for many pharmaceutical compositions it is usual to add at least one antioxidant to prevent degradation and oxidation of the pharmaceutically active ingredients. It will also be understood by those skilled in the art that colorants, flavouring agents and non-therapeutic amounts of other compounds may be included in the formulation.

In one embodiment the antioxidant is selected from the group consisting of tocopherol, deteroxime mesylate, methyl paraben and ascorbic acid.

In yet another embodiment the antioxidant is present in an amount of 1 to 3 g for every litre of water in the formulation. A preferred antioxidant is tocopherol.

In a preferred embodiment at least one protease inhibitor is added to the formulation to inhibit degradation of the pharmaceutical agent by the action of proteolytic enzymes. Of the known protease inhibitors, most are effective at concentrations of from 1 to 3 wt./wt. % of the formulation.

Non-limiting examples of effective protease inhibitors are bacitracin, soyabean trypsin and aprotinin. Bacitracin is the most effective of the three named herein when used in concentrations of from 1.5 to 2.0 wt./wt. %. The other two may be used in concentrations of about 1 to 2 wt./wt. %.

The pharmaceutical agents may be selected from insulin, antigens selected from the group consisting of MMR (mumps, measles and rubella) vaccine, typhoid vaccine, hepatitis A vaccine, hepatitis B vaccine, herpes simplex virus, bacterial toxoids, cholera toxin B-subunit, influenza vaccine virus, bordetela pertussis virus, vaccinia virus, adenovirus, canary pox, polio vaccine virus, plasmodium falciparum, bacillus calmette geurin (BCG), klebsiella pneumoniae, HIV envelop glycoproteins and cytokins and other agents selected from the group consisting of bovine somatropine (sometimes referred to as BST), estrogens, androgens, insulin growth factors (sometimes referred to as IGF), interleukin-I, interleukin-II and cytokins. Three such cytokins are interferon-β, interferon-γ and tuftsin.

Examples of bacterial toxoids are tetanus, diphtheria, pseudomonas A, mycobacterium tuberculosis. Examples of HIV envelop glycoproteins are gp 120 and gp 160 for AIDS vaccines. Examples of anti-ulcer $H_2$ receptor antagonists are ranitidine, cimetidine and famotidine, and other anti-ulcer drugs are omparazide, cesupride and misoprostol. An example of a hypoglycaemic agent is glizipide. Insulin is used for the control of diabetes.

As will be understood by those skilled in the art, two or more pharmaceutical agents may be combined for specific effects. The necessary amounts of active ingredient can be determined by simple experimentation. Specific pharmaceutical agents which are particularly suited to this invention are insulin, heparin, low molecular weight heparin, hirugen, hirulos and huridine.

In a further embodiment the pharmaceutical agent is insulin.

The method of making the formulation is easy. Typically the absorption enhancing compounds are added to cold water and vigorously mixed. The pharmaceutical agent or agents, any antioxidants, inorganic salts, protective polymers, protease inhibitors and other ingredients, e.g. colouring matter, flavourings, are then added and mixed until the solution is homogeneous.

In the selection of a suitable absorption enhancing compound combination, it has been found that the amount of total absorption enhancing compound should be less than about 10 wt./wt. % of the formulation and preferably from 1 to 5 wt./wt. %. Frequent use or prolonged use of higher concentrations of absorption enhancing compounds are likely to be harmful to linings and tissues in the gastrointestinal tract, and may cause diarrhoea. It is believed that the optimum range for most combinations is from 1.5 to 3.5 wt./wt. %

In general, advantages of the present formulation are that adverse reactions are decreased and bioavailability is increased. Furthermore, manufacture of the formulation is simple. Due to the liquid nature of the formulation, ingestion is easy, the action of the pharmaceutical agent can occur very rapidly, e.g. within 10–15 minutes, and the problem of gastric emptying is minimized.

The invention is now exemplified by reference to insulin, although this is not to be taken as limiting. In the case of insulin, oral administration provides for rapid onset of action, gives a long duration of action, is convenient and is free from the discomfiture of injection. In addition, it more closely mimics normal physiological insulin secretion. The present oral insulin may serve as the sole substitution of insulin injection in the case of insulin dependent diabetes mellitus and pharmacologic therapy for non-insulin dependent diabetes mellitus.

The invention is illustrated by the following nonlimiting examples.

EXAMPLE I 0.2 g of chenodeoxycholate, 0.2 g of deoxycholate, 0.2 g polyoxyethylene 9-lauryl ether were dissolved in a small quantity of cold (4° C.) distilled water which contained 0.2% gelatin and 0.9% sodium chloride. Dissolution was effected with rapid stirring, and the volume topped up to 9 ml with distilled water. To this clear suspension was added 1 ml of Novolin-R (trade mark) fast acting insulin. The mixture was stirred continuously to give a homogenous solution. One millilitre aliquots of this solution (10 IU insulin) were then administered orally to diabetic rats according to the following protocol. Several batches were made in order to feed to the number of rats in the study.

Fifty-five genetically diabetic (urine glucose positive) male wistar BB strain rats weighing 300–400 g were used in the study. The rats were grouped in five groups of eleven rats each. The rats were monitored for diabetes by blood glucose testing using an Accucheck-III (trade mark) glucometer. Diabetes was confirmed by severe hyperglycaemia, with blood glucose levels of greater than 30 mmol/L.

At the beginning of the experiment, each rat was numbered and bled for a blood glucose level measurement. Each rat was gavaged with a 1 ml solution containing 3 parts Hanks balanced salt solution to 7 parts sodium bicarbonate to neutralize the stomach acid. One millilitre portions of the oral insulin formulation prepared as above was mixed with 1 ml of saline solution portions and then administered to the rats with a stainless steel gavage tube. One dose was administered per rat per day. Blood was removed via an implanted angiocatheter in a tail vein for determination of serum insulin levels at 0, 2, 5, 10, 15 30, 45, 60, 90 and 120 minutes after administration of the dose. The resultant sera were frozen and sent to a laboratory for analyzing total serum insulin levels by radioimmunoassay. In addition, 10 µl blood samples were drawn from each rat at 0, 30, 60, 120, 180, 240, 300, 360 minutes and 24 hours after administration of the dose, for glucose level analysis. The results for 22 of the rats are shown in Table I, and for 5 of the rats are shown in Table II.

TABLE I

Changes in blood glucose levels (mmol/L):

| Rat | Time (hours) | | | | | | | |
|---|---|---|---|---|---|---|---|---|
| | 0 | 0.5 | 1.0 | 2.0 | 3.0 | 5.0 | 6.0 | 24.0 |
| 1 | 30.0 | 21.2 | 13.1 | 10.3 | 12.4 | 16.5 | 18.2 | 19.7 |
| 2 | 29.5 | 26.0 | 12.8 | 11.0 | 13.1 | 17.4 | 16.9 | 18.1 |
| 3 | 28.7 | 25.5 | 21.5 | 7.7 | 12.8 | 16.1 | 21.8 | 18.5 |
| 4 | 28.0 | 19.1 | 13.4 | 10.1 | 15.3 | 19.8 | 20.8 | 20.0 |
| 5 | 30.8 | 18.0 | 12.1 | 10.0 | 12.3 | 13.0 | 21.7 | 22.2 |
| 6 | 28.6 | 13.2 | 10.1 | 9.2 | 13.4 | 15.3 | 18.8 | 16.1 |
| 7 | 28.9 | 23.4 | 18.0 | 6.2 | 11.8 | 16.6 | 22.6 | 20.6 |
| 8 | 30.1 | 18.3 | 10.4 | 7.2 | 9.6 | 17.1 | 23.2 | 21.3 |
| 9 | 26.8 | 12.1 | 10.7 | 6.9 | 13.8 | 16.8 | 18.7 | 17.0 |
| 10 | 27.3 | 18.1 | 11.5 | 6.4 | 11.4 | 18.1 | 23.2 | 16.2 |
| 11 | 28.7 | 16.6 | 11.2 | 5.1 | 10.0 | 19.1 | 22.0 | 16.0 |
| 12 | 28.0 | 18.0 | 12.8 | 11.6 | 14.3 | 16.8 | 20.2 | 16.0 |
| 13 | 28.8 | 25.2 | 12.5 | 10.3 | 16.4 | 19.1 | 20.4 | 16.2 |
| 14 | 28.0 | 19.1 | 13.4 | 11.1 | 15.5 | 19.7 | 25.6 | 13.0 |
| 15 | 25.8 | 13.2 | 10.1 | 8.7 | 13.0 | 16.1 | 21.7 | 19.3 |
| 16 | 27.7 | 23.4 | 14.1 | 10.8 | 12.4 | 17.0 | 23.7 | 23.9 |
| 17 | 28.3 | 18.3 | 11.1 | 8.2 | 13.4 | 16.2 | 24.8 | 18.6 |
| 18 | 28.8 | 20.9 | 11.4 | 7.8 | 13.0 | 16.6 | 19.2 | 19.2 |
| 19 | 28.0 | 22.3 | 14.3 | 6.9 | 14.5 | 19.3 | 21.3 | 24.8 |
| 20 | 27.1 | 16.0 | 11.2 | 7.7 | 13.6 | 17.9 | 20.4 | 28.0 |
| 21 | 26.8 | 17.5 | 10.1 | 5.7 | 14.3 | 19.2 | 27.7 | 28.0 |
| 22 | 27.3 | 14.2 | 12.5 | 6.9 | 11.4 | 23.3 | 27.8 | 27.9 |

TABLE II

Plasma insulin levels (µU/ml):

| Rat | | 23 | 24 | 25 | 26 | 27 |
|---|---|---|---|---|---|---|
| Time mins | 5 | 15.2 | 12.1 | 16.7 | 14.2 | 13.8 |
| | 7 | 48.3 | 37.5 | 43.3 | 40.6 | 42.9 |

TABLE II-continued

Plasma insulin levels (µU/ml):

| Rat | 23 | 24 | 25 | 26 | 27 |
|---|---|---|---|---|---|
| 10 | 54.7 | 52.8 | 55.6 | 49.5 | 52.8 |
| 15 | 52.6 | 45.2 | 50.5 | 48.7 | 51.1 |
| 30 | 32.0 | 35.3 | 31.0 | 28.7 | 30.2 |
| 45 | 19.2 | 12.2 | 12.5 | 11.8 | 12.3 |
| 60 | 7.7 | 5.8 | 4.0 | 5.1 | 4.1 |
| 90 | 3.5 | 4.4 | 2.1 | 3.2 | 3.3 |
| 120 | 2.0 | 2.8 | 1.6 | 1.9 | 2.5 |

Table I shows that the orally administered insulin formulation has a metabolic effect on the blood glucose levels. It is clear that within 2 hours the blood glucose level reached a normal level (7 mmol/L) from an initial level of about 30 mmol/L. The onset of action was very fast, i.e. about 10 minutes after administration and maximum serum level was achieved within 15 minutes and the effect lasted for 24 hours with a single dose of the oral insulin formulation.

EXAMPLE II

For comparative purposes, a composition containing only one absorption enhancer was tested. A composition comprising 0.3 g sodium cholate, 0.2 soyabean trypsin inhibitor, 16 IU insulin, 8.4 ml saline solution and 0.2 g polyethylene glycol in 10 ml of distilled water was prepared. The composition is not within the scope of the present invention. The procedure of Example I was followed and 1 ml aliquots were gavaged to rats. 10 µl blood samples were drawn from each rat at 0 mins, 30 mins, 1, 2, 3, 4 and 24 hours after administration of the dose, for glucose level analysis. The results are shown in Table III.

TABLE III

Changes in blood glucose levels (mmol/L):

| Rat | Time (hours) | | | | | | |
|---|---|---|---|---|---|---|---|
| | 0.0 | 0.5 | 1.0 | 2.0 | 3.0 | 4.0 | 24.0 |
| 31 | 30.3 | 28.5 | 26.0 | 28.0 | 20.1 | 15.8 | 28.0 |
| 32 | 28.5 | 28.0 | 27.1 | 25.0 | 28.0 | 21.7 | 28.0 |
| 33 | 29.0 | 28.0 | 26.0 | 28.1 | 28.0 | 24.2 | 28.2 |
| 34 | 28.7 | 28.1 | 26.5 | 23.0 | 26.9 | 23.0 | 29.6 |
| 35 | 27.8 | 28.2 | 28.0 | 24.1 | 21.3 | 18.2 | 30.3 |
| 36 | 28.9 | 27.5 | 28.0 | 20.5 | 21.5 | 23.8 | 28.0 |
| 37 | 28.1 | 28.2 | 26.5 | 24.0 | 27.5 | 28.0 | 29.2 |
| 38 | 28.9 | 26.8 | 24.0 | 19.0 | 20.2 | 21.8 | 29.7 |

Table III shows that the orally administered insulin formulation which contains only one absorption enhancer, i.e sodium cholate, has very little metabolic effect on the blood glucose levels.

EXAMPLE III 0.25 g of oleic acid, 0.25 g of linoleic acid, 0.1 g sodium lauryl sulphate and 0.25 ml of Tween® 80 polyoxyethylene sorbitan ester were dissolved in a small quantity of cold (4° C.) distilled water which contained 0.2% gelatin and 0.9% sodium chloride. Dissolution was effected with rapid stirring, and the volume topped up to 9 ml with distilled water. To this clear suspension was added 1 ml of Novolin-R (trade mark) fast acting insulin. The mixture was stirred continuously to give a homogenous solution.

Aliquots of the solution were administered to diabetic (urine glucose positive) male wistar BB strain rats as in Example I and blood glucose levels were determined at intervals of 0 min, 30 min, 1, 2, 3 and 5 hours after administration of the dose. The results are shown in Table IV.

TABLE IV

| | Changes in blood glucose levels (mmol/L): | | | | | |
|---|---|---|---|---|---|---|
| | Time (hours) | | | | | |
| Rat | 0.0 | 0.5 | 1.0 | 2.0 | 3.0 | 5.0 |
| 41 | 28.5 | 21.8 | 11.8 | 8.9 | 13.2 | 12.6 |
| 42 | 29.0 | 18.3 | 18.0 | 13.2 | 12.8 | 14.8 |
| 43 | 28.7 | 12.0 | 8.7 | 9.8 | 11.4 | 13.4 |
| 44 | 30.1 | 18.1 | 10.4 | 8.8 | 13.8 | 25.6 |

EXAMPLE IV

The experiment of Example III was repeated, except that the composition comprised 0.25 g of disodium EDTA, 0.25 g of sodium salicylate and 0.25 g of polyoxyethylene 9-lauryl ether dissolved in a small quantity of cold (4° C.) distilled water which contained 0.2% gelatin and 0.9% sodium chloride. The results are shown in Table V below.

TABLE V

| | Changes in blood cilucose levels (mmol/L): | | | | | |
|---|---|---|---|---|---|---|
| | Time (hours) | | | | | |
| Rat | 0.0 | 0.5 | 1.0 | 2.0 | 3.0 | 5.0 |
| 51 | 28.6 | 28.1 | 17.9 | 15.2 | 13.8 | 25.0 |
| 52 | 29.8 | 16.1 | 13.0 | 11.8 | 12.2 | 18.2 |
| 53 | 29.6 | 17.0 | 10.3 | 10.1 | 15.1 | 23.7 |
| 54 | 30.1 | 11.4 | 11.5 | 9.9 | 11.8 | 15.3 |

EXAMPLE V

The experiment of Example III was repeated, except that the composition comprised 0.1 g of monoolein, 0.25 g of deoxycholate and 0.25 g of polyoxyethylene 9-lauryl ether dissolved in a small quantity of cold (4° C.) distilled water which contained 0.2% gelatin and 0.9% sodium chloride. The results are shown in Table VI.

TABLE VI

| | Changes in blood glucose levels (mmol/L | | | | | |
|---|---|---|---|---|---|---|
| | Time (hours) | | | | | |
| Rat | 0.0 | 0.5 | 1.0 | 2.0 | 3.0 | 5.0 |
| 61 | 28.1 | 14.5 | 11.2 | 10.2 | 10.3 | 14.3 |
| 62 | 28.0 | 26.0 | 21.9 | 12.2 | 8.0 | 15.8 |
| 63 | 29.8 | 24.3 | 20.0 | 15.4 | 12.8 | 14.2 |
| 64 | 29.5 | 18.4 | 14.2 | 10.2 | 11.0 | 17.0 |

Examples III, IV and V all show the metabolic effect on the blood glucose levels of the orally administered insulin.

We claim:

1. A liquid pharmaceutical agent formulation suitable for oral or nasal delivery comprising a proteinic pharmaceutical agent, water and at least two absorption enhancing compounds, wherein said absorption enhancing compounds are selected from the group consisting of a combination of deoxycholate, chenodeoxycholate, and polyoxyethylene 9-lauryl ether, a combination of sodium salicylate, deoxycholate, chenodeoxycholate, and polyoxyethylene 9-lauryl ether, a combination of sodium deoxycholate, chenodeoxycholate, polyoxyethylene 9-lauryl ether and monoolein, a combination of deoxycholate, chenodeoxycholate and sodium salicylate, a combination of deoxycholate, sodium salicylate and sodium lauryl sulphate, a combination of oleic acid, linoleic acid and sodium lauryl sulphate, a combination of monoolein, deoxycholate and polyoxyethylene 9-lauryl ether, a combination of deoxycholate, chenodeoxycholate, polyoxyethylene 9-lauryl ether and sodium tauro-24, 25-dihydrofusidate, a combination of sodium deoxycholate, chenodeoxycholate, polyoxyethylene 9-lauryl ether and sodium tauro-24, 25-dihydrofusidate, a combination of deoxycholate, chenodeoxycholate, taurodeoxycholate, polyoxyethylene 9-lauryl ether and monoolein, a combination of chenodeoxycholate, glycochenodeoxycholate, polyoxyethylene 9-lauryl ether and sodium tauro-24, 25-dihydrofusidate, a combination of chenodeoxycholate, sodium lauryl sulphate and disodium EDTA, a combination of deoxycholate, chenodeoxycholate, polyoxyethylene 9-lauryl ether and disodium EDTA, a combination of sodium salicylate, disodium EDTA and polyoxyethylene 9-lauryl ether, a combination of monoolein, oleic acid and polyoxyethylene sorbitan ester, a combination of monoolein, oleic acid, polyoxyethylene sorbitan ester and sodium lauryl sulphate, and a combination of linoleic acid, monoolein and sodium salicylate, wherein the amount of each of the absorption enhancing compounds is present in a concentration of from 1 to 10 wt./wt. % of the total formulation.

2. A liquid pharmaceutical agent formulation according to claim 1 wherein the absorption enhancing compound compositions are selected from the group consisting of i) a combination of deoxycholate, chenodeoxycholate and sodium salicylate, ii) a combination of sodium salicylate, deoxycholate and sodium lauryl sulphate, iii) a combination of chenodeoxycholate, sodium lauryl sulphate and disodium EDTA and iv) a combination of monoolein, oleic acid and polyoxyethylene sorbitan ester, and v) a combination of deoxycholate, chenodeoxycholate and polyoxyethylene 9-lauryl ether.

3. A liquid pharmaceutical agent formulation according to claim 1 wherein the formulation contains at least one protective polymer for slow release of the pharmaceutical agent.

4. A liquid pharmaceutical agent formulation according to claim 1 wherein the formulation contains at least one protective polymer selected from the group consisting of polyvinyl alcohol, polyethylene glycol and gelatin.

5. A liquid pharmaceutical agent formulation according to claim 1 wherein the formulation contains an antioxidant.

6. A liquid pharmaceutical agent formulation according to claim 1 wherein the formulation contains an antioxidant selected from the group consisting of tocopherol, deteroxime mesylate, methyl paraben and ascorbic acid.

7. A liquid pharmaceutical agent formulation according to claim 1 wherein the formulation contains at least one protease inhibitor.

8. A liquid pharmaceutical agent formulation according to claim 1 wherein the formulation contains a protease inhibitor selected from the group consisting of bacitracin, soyabean trypsin and aprotinin in a concentration of from 1 to 3 wt./wt. %.

9. A liquid pharmaceutical agent formulation according to claim 1 wherein the pharmaceutical agent is selected from the group consisting of insulin, heparin, hirugen, hirulos, huridine, mumps, measles and rubella vaccine, typhoid vaccine, hepatitis A vaccine, hepatitis B vaccine, herpes simplex virus, bacterial toxoids, cholera toxin B-subunit, influenza vaccine virus, bordetala pertussis, vaccinia virus, adenovirus, canary pox, polio vaccine virus, plasmodium falciparum, bacillus calmette geurin (BCG), klebsiella pneumoniae, HIV envelop glycoproteins, bovine somatropine, estrogens, androgens, insulin growth factors, interleukin-I, interleukin-II and cytokins.

10. A liquid insulin formulation according to claim 1 wherein the pharmaceutical agent is insulin.

11. A liquid insulin formulation according to claim 10 wherein the formulation also contains at least one inorganic salt which opens channels in the gastrointestinal tract, at least one protective polymer and at least one protease inhibitor.

12. A liquid insulin formulation according to claim 11 wherein the inorganic salt is selected from the group consisting of sodium chloride, potassium chloride, calcium chloride, zinc chloride and sodium bicarbonate, the protective polymer is selected from the group consisting of polyvinyl alcohol, polyethylene glycol and gelatin, and the protease inhibitor is selected from the group consisting of bacitracin, soyabean trypsin and aprotinin.

13. A liquid insulin formulation according to claim 12 which also contains an antioxidant.

* * * * *